US007685012B2

(12) United States Patent
Wilson

(10) Patent No.: US 7,685,012 B2
(45) Date of Patent: *Mar. 23, 2010

(54) METHOD AND SYSTEM FOR ANALYZING RESOURCE ALLOCATION BASED ON COHORT TIMES

(76) Inventor: Thomas W. Wilson, 809 Almahurst La., Loveland, OH (US) 45140

( * ) Notice: Subject to any disclaimer, the term of this patent is extended or adjusted under 35 U.S.C. 154(b) by 1409 days.

This patent is subject to a terminal disclaimer.

(21) Appl. No.: 10/748,730

(22) Filed: Dec. 30, 2003

(65) Prior Publication Data

US 2005/0144051 A1    Jun. 30, 2005

(51) Int. Cl.
    *G06F 17/50* (2006.01)
(52) U.S. Cl. ............... 705/7; 705/8; 705/2; 705/500
(58) Field of Classification Search ............ 705/7
    See application file for complete search history.

(56) References Cited

U.S. PATENT DOCUMENTS

| | | | | |
|---|---|---|---|---|
| 5,692,125 | A * | 11/1997 | Schloss et al. | 705/9 |
| 5,891,868 | A * | 4/1999 | Cummings et al. | 514/178 |
| 5,976,082 | A * | 11/1999 | Wong et al. | 600/300 |
| 5,991,733 | A * | 11/1999 | Aleia et al. | 705/8 |
| 6,223,164 | B1 * | 4/2001 | Seare et al. | 705/2 |
| 2003/0065534 | A1 * | 4/2003 | McCartney | 705/2 |

OTHER PUBLICATIONS

Rohrer, J.E. "Duration of heart disease visits by elderly patients: productivity versus quality" Health Services Management Research, Aug. 2002, p. 141-146.* http://www.phiinstitute.org/evaluation.html (4 of 4)Jan. 4, 2008 3:40:51 PM.*

Lynch, John W. et al. "Childhood and adult socioeconomic status as predictors of mortality in Finland" , The Lancet, Feb. 26, 1994, p. 524.*

Wilson, Thomas; "Evaluating ROI in State Disease Management Programs" State Coverage Initiatives, vol. IV, No. 5, Nov. 2003.*

Geskus, R. "Methods for estimating the AIDS incubation time distribution when date of seroconversion is censored" (2001), Statistics in Medicine, Statist. Med. 2001; 20:795-812.*

Gordin, Fred, et al. "Early Manifestations of Disseminated *Mycobacterium avium* Complex Disease: A Prospective Evaluation", The Journal of Infectious Diseases 1997;176:126-32 by The University of Chicago.*

(Continued)

*Primary Examiner*—Scott L Jarrett
*Assistant Examiner*—Mark A Fleischer
(74) *Attorney, Agent, or Firm*—Mark F. Smith; Smith Brandenburg Ltd

(57) ABSTRACT

The present invention is a method for improving resource allocation comprising the steps of identifying at least one criteria; Identifying sets of information wherein each set of information includes a unique unit of analysis (UOA-ID), a calendar/clock time (CCT), a CATVAR and a VAR Value; grouping each UOA-ID into an appropriate specific population (Type); identifying a Start Time wherein each UOA-ID has met said at least one criteria; forming at least one prospective or retrospective Cohort time segment for each UOA-ID based on their Start Time; placing the UOA-ID into the appropriate time segment; calculating an eligibility score for each UOA-ID for each time segment; calculating an Eligible Adjusted Variable Value; and generating at least one Output Expression.

26 Claims, 7 Drawing Sheets

OTHER PUBLICATIONS

Goggins, William, et al. "Applying the Cox Proportional Hazards Model for Analysis of Latency Data With Interval Censoring", Statistics in Medicine Statist. Med. 18, 2737-2747 (1999).*

Kim, S. et al. "Strategies for Cohort Sampling Under the Cox Proportional Hazards Model, Application to an AIDS Clinical Trial", Lifetime Data Analysis, 5, 149-172 (1999) Kluwer Academic Publishers, Boston. Manufactured in The Netherlands.*

* cited by examiner

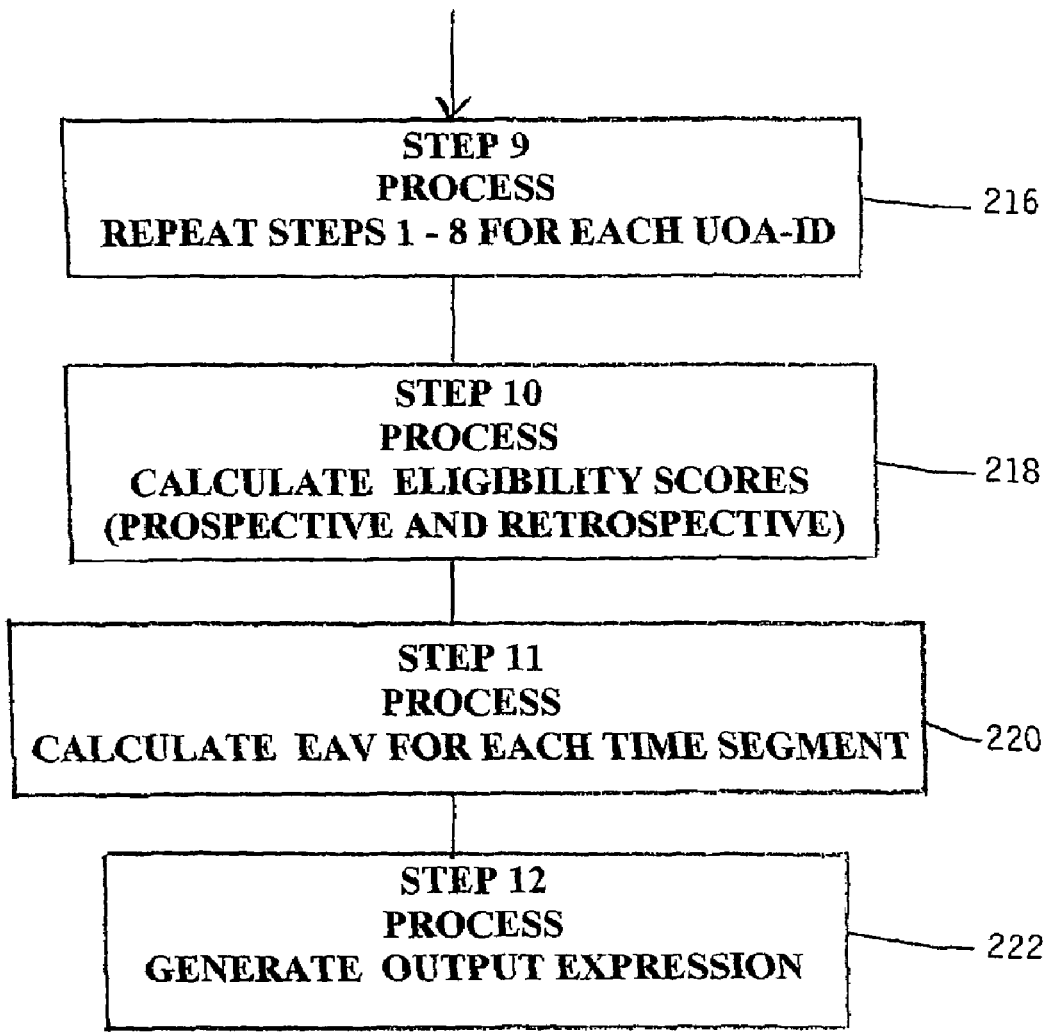

METHOD AND SYSTEM FOR ANALYZING RESOURCE ALLOCATION BASED ON COHORT TIMES

TECHNICAL FIELD

The present invention related to a method and system for allocating resources to achieve specified outcomes and, more particularly, to a method and system for analyzing data for allocating resources over time for defined populations to achieve specified outcomes to best serve a business' goals.

BACKGROUND OF THE INVENTION

Managing a business or an organization in a manner that creates long term value is a complex activity. Further, every business or organization has limited resources and the need for business to accurately monitor their costs and justify resource allocation to achieve specified outcomes in a future calendar time period (e.g., financial quarters) is becoming increasingly important. Unfortunately, the task of organizing business information to determine proper resource allocation is often extensive and troublesome to organize and it is often difficult or impossible for business managers to use this information to make proper decisions. Accordingly, businesses and other organizations typically either overspend their resources or do not avail themselves of statistical data and analysis that can be used to optimize their resource expenditures. For example, business establishments that serve a large number of customers generally have a problem analyzing their transactional information to develop trends in defined population over time. Such trends are desirable to effectively target and determine the effectiveness of various programs for the purposes of optimizing resource allocation to achieve specified outcomes over designed time periods. Further, while it may be known that certain cost reduction programs are hypothesized to be effective to reduce future costs, a need exists for an effective and scientific method and system for optimizing resource allocation that can be shown to achieve specified outcomes over time to maximize a business's investment.

Until now, most economic business models have relied on "calendar time" in determining resource allocation rather than using "experience time" where time is based on the start of an event and its duration (such as the day one purchased a car or the date/time an individual was bitten by a malarial infected mosquito, starting the individual on a "natural" course of fluctuating fevers). Thus, the experience of a population in any calendar time period will vary depending on when each individual "started" in this population. Accordingly, a business organization will be better able to analyze and evaluate the resources that will be necessary to achieve a specific outcome by first understanding this "Cohort Time" heterogeneity of any population during any calendar (or clock) time period.

By way of illustration, manufactures, such as automobile manufactures, are actively searching for ways to reduce the probability of realizing extensive repair costs under warranty. Despite dramatic improvement in new-vehicle quality at most major automobile manufacturers over the past decade, the reduction of warranty cost is a large area for potential cost reductions. While manufactures have developed sophisticated statistical tracking systems, until now there was no adequate method or system to assess available resources today to reduce specified outcomes (i.e., warranty costs) in the future.

Recently, the optimization of resource allocation has become particularly important for businesses engaged in the health care industry. Due to significant increases in health care costs, health care providers and service management organizations have become under increased pressure by customers to find ways of lowering or at least slow the rate of growth of health care costs. As a result of such pressure, health care providers have implemented numerous population-based programs, such as wellness programs, disease management programs, and other health-inducing and cost-reduction programs, designed to improve the overall health of the population thereby reducing, at least theoretically, overall health care costs. Such health care organizations, however, are in need of a system that can qualitatively analyze program performance in order to optimize allocation of health care services and expenditures over time to achieve specified outcomes.

Accordingly, a need exist for a method and system to qualitatively analyze cost reduction programs and for analyzing information for allocating resources to best serve a business' goals. In health care and product warranty work, the ventral issues are the same. An "individual unit" with a certain characteristic that makes it eligible for inclusion in a defined population, is entered into the population at a certain "start time" (clock or calendar time) and remains "eligible" for this population during a known and quantifiable duration of time. Furthermore, this population has a greater than zero probability of experiencing some event at a future time period, an event with some economic value attached to it. This event, the "individual unit," the date of the event, and the "cash value" of such event is captured by a transaction system. The method and apparatus transforms this information into usable estimates for resource allocation decisions needed to achieve specified outcomes.

DISCLOSURE OF THE INVENTION

The present invention provides a method for analyzing resource allocation. In a preferred embodiment of the invention the method uses a set of information, and comprises the steps of identifying an Unit of Analysis Identifier, a Type, a clock or calendar time and a Variable Value for each set of information; grouping and organizing each Unit of Analysis Identifier into an appropriate Type; identifying a Start Time; identifying a time segment period; forming time segments based on the Start Time; adjusting.(e.g. for economic inflation) and standardizing (e.g. for actual eligibility) each Variable Value to create Adjusted Variable Values; placing each Adjusted Variable Value into the appropriate time segment; calculate an eligibility-adjusted score for each Unit of Analysis Identifier for each time segment; and generating an Output Expression.

In another preferred embodiment of the invention the method further comprises the step of transforming the Output Expression from being expressed in Cohort time segments to being expressed in CCT segments.

In another embodiment of the invention the method for analyzing resource allocation is performed using a system comprising a central processing unit for implementing system software effective for performing the method.

In another preferred embodiment of the invention the method for analyzing resource allocation is used for marketing studies.

In another preferred embodiment of the invention the method for analyzing resource allocation is used for trademark evaluation.

In another preferred embodiment of the invention the method for analyzing resource allocation is used for analyzing the effects of similar trademarks.

In another preferred embodiment of the invention the method for analyzing resource allocation is used for warranty studies.

In another preferred embodiment of the invention the method for analyzing resource allocation is used for health care studies.

In another preferred embodiment of the invention the method for analyzing resource allocation is used for applications selected from the group consisting of actuarial applications, insurance applications, marketing and advertising applications, frequent use program applications, shopping card applications, trademark/trade dress/product design evaluation applications, web page applications, infringement applications, and health care applications.

Another preferred embodiment of the invention, a system for analyzing resource allocation comprises a central processing unit for operating software effective for performing the method of grouping data identified by the user into appropriate Groupers (Grouper can be equivalent to type, in that case it is a many-to-few algorithm); identifying a Start Time; forming at least one Cohort time segment based on the Start Time; adjusting and standardizing the information and placing the information into the appropriate time segment; calculating an eligibility score for the information for each time segment, and generating at least one Output Expression.

In another embodiment of the invention, the system for analyzing resource allocation is used for marketing studies.

In another embodiment of the invention, the system for analyzing resource allocation is used for trademark evaluation.

In another embodiment of the invention, the system for analyzing resource allocation is used for analyzing the effects of similar trademarks.

In another embodiment of the invention, the system for analyzing resource allocation is used for warranty studies.

In another preferred embodiment of the invention, the system for analyzing resource allocation is used for health care studies.

Another preferred embodiment of the invention is an Output Expression for use in analyzing resource allocation comprising a representation showing trends of a particular Population, said trends are expressed in Cohort time segments.

In another preferred embodiment of the invention, an Output Expression is generated by the method comprising the step of calculating an Eligible Adjusted Variable Value ("EAV") based on a summary metric for each Individual Unit of Analysis ("UOA-ID") per Type.

In another preferred embodiment of the invention, an Output Expression is generated by the method comprising the steps of determining a dichotomous variable ("DV") per Type per time segment; calculating a EAV summary metric for all UOA-IDs per Type per time. segment; and calculating an EAV Net Value per Type per time segment.

In another preferred embodiment of the invention the Output Expression is generated by the method comprising the steps of determining a return on resource allocation ("RORA"); determining an Outcome; calculating a number needed to target ("NNT"); calculating an EAV Net Value per Type per time segment; and calculating the maximum available resource allocation ("RA") per UOA-ID per time segment.

In another preferred embodiment of the invention the Output Expression is generated by the method comprising the steps of determining a RA and an Outcome, calculating a NNT, calculating an EAV Net value per Type per time segment and calculating the RORA.

In another preferred embodiment of the invention the Output Expression is generate by the method comprising the steps of determining a RA and a RORA, calculating a NNT, calculating an EAV Net value per Type per time segment and calculating the Outcome.

Another preferred embodiment of the invention is a method of analyzing the effects of similar trademarks;

Another preferred embodiment of the invention is a method of analyzing and evaluating resource allocation for the health care industry, Another preferred embodiment of the invention is a method of allocating resources for use in marketing;

Other advantages of the invention will be apparent from the following description, the accompanying drawings and the appended claims.

BRIEF DESCRIPTION OF THE DRAWINGS

To provide a more complete understanding of the present invention and further features and advantages thereof, reference is now made to the following description taken in conjunction with the accompanying drawings, in which:

FIGS. 3a and 3b is a flow diagram illustrating the general functional steps of the system of FIG. 1;

BEST MODE FOR CARRYING OUT THE INVENTION

Figure 1:
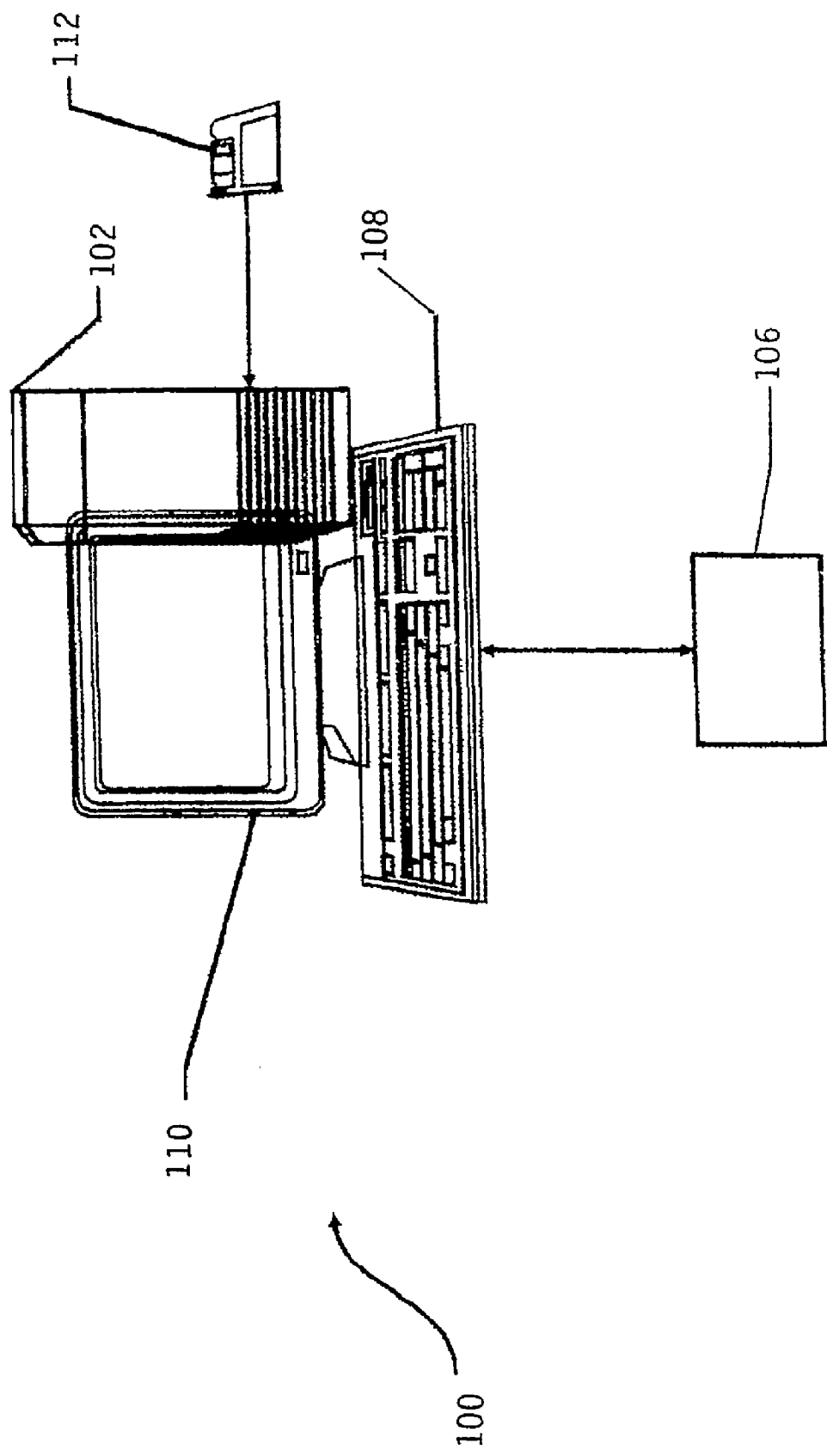
FIG. 1 is a diagrammatic representation of a system for providing a method of resource allocation in accordance with the present invention.

The present invention relates to a method and system for analyzing resource allocation. In describing the preferred embodiments of the invention illustrated in the drawings, specific terminology will be resorted to for the sake of clarity. However, the invention is not intended to be limited to the specific terms so selected, and it is to be understood that each specific term includes all technical equivalents that operate in a similar manner to accomplish a similar purpose.

Referring to FIG. 1, a preferred embodiment of the system 100 for providing a method of resource allocation the present invention is shown comprising a central processing unit 102 used to implement the system software 104 (FIG. 2) of the system 100. The central processing unit 102 includes a memory 106 and may be coupled to other devices, such as a suitable input device 108, like a keypad, touch screen, or any other suitable input device that can accept information, and one or more suitable output devices 110, such as a computer or electronic display device, printer, projection device, and the like. It should be understood that the system 100 could include any combination of the above components, or any number of different components peripherals, and other devices. Preferably, the central processing unit 102 operates under the control of an operating system, such as the WINDOWS™ operating system developed by Microsoft Corporation or the Macintosh™ operating system developed by Apple Computer Corporation or other "mainframe" operating system It should be understood, however, that other operating systems could be utilized to implement the system software 102 (FIG. 2) of the system 100 of the present invention.

The system software 104 is a computer-readable medium having computer-readable instructions for performing the method of optimizing resource allocation. Preferably, the system software 104 is an interactive, menu and event driven system that uses prompt, dialog, and entry windows to guide a user to enter information. As used herein, the term "software" refers to any form of programmed machine-readable language or instructions (e.g., object code) that, when loaded or otherwise installed, provides operating instructions to a machine capable of reading those instructions, such as a computer. The system software 104 of the present invention can be stored or reside on, as well as be loaded or installed from, various software input devices 112 such as one or more floppy disks, CD ROMS disks, hard disks or any other form of suitable non-volatile electronic storage media. The system software 104 can also be installed by downloading or other form of remote transmission, such as by using Local or Wide Area Network (LAN or WAN)-based, Internet-based, web-based or other remote downloading or transmission methods. Upon a user's entry of appropriate initialization commands entered via the input device 108, the system software 104 is read by the central processing unit 102 and the method of the present invention for optimizing resource allocation is implemented.

Figure 2:
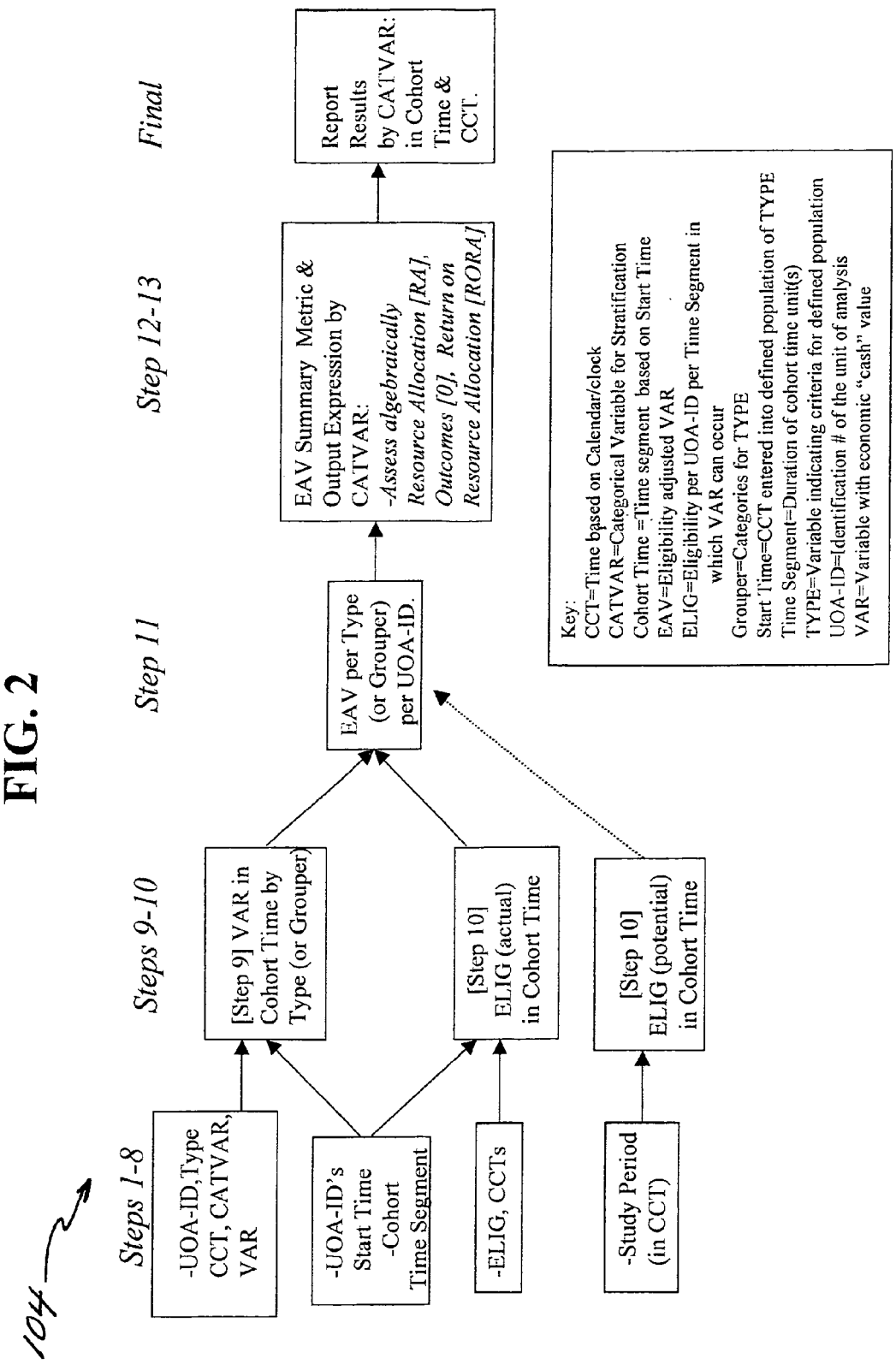
FIG. 2 is a diagrammatic representation showing the general methodology of the present invention.
Figure 3A:
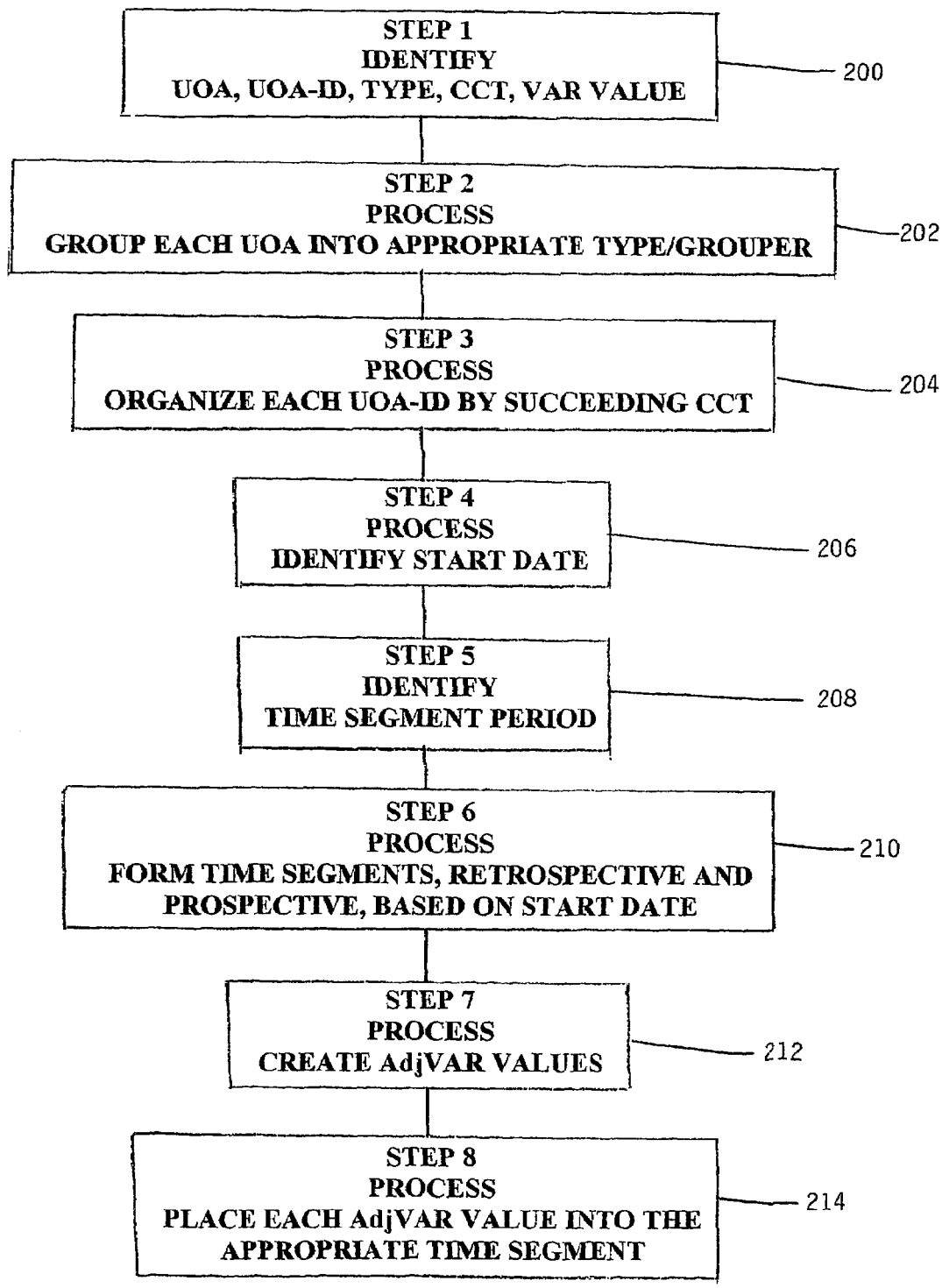

Referring to FIGS. 1, 2 and 3, a flowchart illustrating the overall structured methodology and design of the system software 104 of the present invention is shown. In a preferred embodiment of the invention, a set of information comprising the unit of analysis ("UOA"), the identification of their particular UOA ("UOA-ID"), the Type, and the calendar clock date/time ("CCT") are identified (step 1) 200 by the system user (not shown) is stored in the information data bank, as represented by Table 1, within the memory 106 of the CPU 102. As used herein, the term "Unit of Analysis" means the basic or minimum analytical unit that is to be examined using the method and system of the present invention. The term "UOA-ID" means the particular individual UOA entity involved in the study. For example, in the retail industry, the UOA can be, but are not limited to, an individual person, an individual product line, individual type of person, store type or a section of a store, office type, etc. For the heath care industry for example, the UOA can be, but are not limited to, patients having a common diagnosis or condition, medical offices, hospital units, hospitals, etc. Preferably, the UOA will be the most basic analytic unit that can be supported by the known information. The "UOA-ID" can include, but are not be limited to, an individual product, an individual person, an individual store, office, etc. For the health care industry for example, the UOA-ID can include, but are not limited to, an individual patient, medical office, hospital, or hospital unit. As used herein, the term "Type" means an event or action that operates as a trigger such that when the UOA-ID meets a given criteria it is included into a specific Population. Thus, "Type" refers specifically to the variable that will be used to direct the UOA-ID into a defined Population. For example, "Type" can include, but is not limited to, a specific diagnosis, or the performance of a specific procedure. As used herein, the term "Population" means a defined set comprising at least two or more UOA-IDs that meet an eligibility criteria (e.g. Type) selected for inclusion into the set.

TABLE 1

STEP 1 INPUT INFORMATION

| UOA | UOA-ID | Type | VAR VALUE | CCT |
|---|---|---|---|---|
| Individual | 123 | A | 100 | 15JAN2000 |
| Individual | 123 | B | 200 | 01MAR2000 |
| Individual | 123 | D | 5000 | 15MAR2000 |
| Individual | 124 | C | 500 | 01APR2000 |

A Variable Value ("VAR Value") is also inputted in step 1 200 by the user and is stored in the information data bank. As used herein, the "VAR Value" is a quantity variable or a value and can include, but is not limited to, a quantity count, a dollar value or economic value, the number of products, number of events, etc. As used herein the CCT shall refer to the clock or calendar time at which the transaction of "VAR Value" takes place.

After entering the information in step 1 200, the user also identifies and enters the particular Type to be used to group each UOA. The system software 104 then operates (step 2) 202 to group each UOA-ID into an appropriate "Grouper" (This could be equivalent to a Type or could be derived from an algorithm that turns "many" into "few" which, as represented in Table 2, is then stored in separate Grouper "K" data files in the information data bank. "Grouper" algorithms that can be utilized by the software 104 to turn "many" into "few" are well known and can be proprietary, public, or custom built. For example, UOA-IDs, such as brands of like products (e.g. brands of toothpaste), can be grouped into a generic Grouper called "toothpaste." UOA-IDs, such as brands of cereal can be grouped into a generic Grouper called "cereal" or may be further grouped according to the size of the box of the cereal. In the health care industry, UOA-IDs, such as the 10,000+ codes used by health care providers on transaction/claim forms (ICD-9 codes) can be grouped into Groupers of genus and species type classification. For example see U.S. Pat. Nos. 5,835,897 and 6,223,164.

TABLE 2

STEP 2: GROUP EACH UOA-ID INTO APPROPRIATE GROUPER AND STORE INTO SEPARATE GROUPER "K" FILES

| UOA-ID | Type | CCT | Grouper |
|---|---|---|---|
| 123 | A | 15JAN2000 | X |
| 123 | B | 06FEB2000 | X |
| 124 | C | 01APR2000 | X |
| 123 | D | 10MAR2000 | Y |

Once the various Groupers have been formed, the software 104 operates to organize each UOA-ID, as represented by Table 3, within each Grouper "K" data file by succeeding CCT (step 3) 204 beginning with the earliest CCT thereby creating a virtual date field. The software 104 then operates to identify a "Start Time" which is the earliest CCT for each specific UOA-ID per Type (step 4) 206.

TABLE 3

STEP 4: IDENTIFY START TIME

| UOA-ID | Type | Start Time | Grouper |
|---|---|---|---|
| 123 | A | 15JAN2000 | X |
| 124 | C | 01APR2000 | X |

TABLE 3-continued

STEP 4: IDENTIFY START TIME

| UOA-ID | Type | Start Date | Grouper |
|--------|------|------------|---------|
| 123    | D    | 01APR2000  | Y       |

The user then selects and inputs a time segment period (step 5) 208 which the software 104 operates to form a plurality of time segments ("TS"), retrospective ("−") and prospective ("+"), based on the Start Time, as represented by Table 4, and each having some duration (step 6) 210. It should be understood that the duration can be of any length, e.g. based on days of the month which varies; however, preferably the duration is equal to the selected initial time segment period, also called the "Index Time Segment" as interpretation of findings may be easier. However, it may be more desirable in certain studies to use a calendar month, regardless of its duration, as a definition of a time segment. In that case, some cohort months would have UOA-IDs with "days" ranging from 28 to 31 days, as illustrated in tables 4-13.

TABLE 4

STEP 6: FORM TIME SEGMENTS FOR EACH UOA-ID
(PROSPECTIVE + AND RETROSPECTIVE), BASED ON START TIME.

| UOA-ID | Type | Start Time | Grouper | TS − 2 | TS − 1 (Index) | TS + 1 | TS + 2 |
|--------|------|------------|---------|--------|----------------|--------|--------|
| 123    | A    | 15JAN2000  | X       | .      | .              | .      | .      |
| 124    | C    | 01APR2000  | X       | .      | .              | .      | .      |
| 123    | D    | 01APR2000  | Y       | .      | .              | .      | .      |

Where "." = missing value
Where TS = 30 days in duration (only showing two TS prospectively ("+") and two TS retrospectively ("−"))

As shown VAR Values that have been inputted and stored in the information data bank is then operated on by the system software 104 (step 7) 212 to mathematically adjust and standardized each VAR Value to create Adjusted Variable Values ("AdjVAR Values"), as represented by Table 5. For example, cost or purchase price of a product can be adjusted for inflation rates, premium pricing for a particular business plan, or any other adjustments deemed necessary by the user. It should be understood that the adjustment criterion is selected by the user and is important to enable the information to be properly compared.

TABLE 5

STEP 7: ADJUST AND STANDARDIZE EACH
VAR VALUE TO CREATE AdjVAR VALUES

| UOA-ID | Type | AdjVAR VALUES* | CCT       |
|--------|------|----------------|-----------|
| 123    | A    | 100            | 15JAN2000 |
| 123    | B    | 204            | 01MAR2000 |

TABLE 5-continued

STEP 7: ADJUST AND STANDARDIZE EACH
VAR VALUE TO CREATE AdjVAR VALUES

| UOA-ID | Type | AdjVAR VALUES* | CCT       |
|--------|------|----------------|-----------|
| 123    | D    | 5100           | 10MAR2000 |
| 124    | C    | 515            | 01APR2000 |

Note:
Inflation adjusted to JAN2000 dollars (multiply VAR by adjustment per calendar month to derive AdjVAR Values).
JAN ADJUSTMENT = 1.0, FEB2000 = 1.01, MAR2000 = 1.02, APR2000 = 1.03

The AdjVAR Values are then stored (step 8) 214 in the information data bank for the appropriate time segment, as represented by Table 5. In this way, VAR Values are changed from being tracked by calendar time to Cohort Time. As used herein "Cohort Time" means that the Start Time is based on a defining event, which is the last date/clock time that the individual UOA-ID meets all of the eligibility criteria to be included into the population. Thus, in Cohort Time, the start of TS+1 (Index month) will be the date or time all of the eligibility criteria is met per UOA-ID, not the calendar date or time the resource allocation study begins. For example, an individual ("first individual") who became eligible for a study on Jan. 1, 2001 and participated until Dec. 31, 2001 would have one year of participation. Another individual ("second individual") who started on Dec. 1, 2001 would have one month of experience during the study time from Jan. 1, 2001 to Dec. 31, 2001. In a month-based Cohort Time, the first individual first month would be Jan. 1-31, 2001, and the second individual's first month would be Dec. 1-31, 2001. Thus, in Cohort Time, however, both individuals would be counted in month 1, however, in months 2 to 12, the first individual would be counted while the second individual would not be counted.

After the AdjVAR Values have been sorted and placed in appropriate time segments in step 8 314, as represented in Table 6, the process (steps 1-8) is repeated (step 9) 216 for each UOA-ID.

TABLE 6

STEP 8: Sort and place each AdjVAR for each UOA-ID into the appropriate Time Segment (TS)

| UOA-ID | Type | Start Time | Grouper | TS − 2 | TS − 1 | TS + 1 | TS + 2 |
|---|---|---|---|---|---|---|---|
| 123 | A | 15JAN2000 | X | . | . | 100 | 5100 |
| 124 | C | 01APR2000 | X | . | . | 515 | . |
| 123 | D | 01APR2000 | Y | 100 | 5100 | . | . |

After step 9 216 is complete, eligibility scores (Potential Eligibility Scores and Actual Eligibility Scores), prospective and retrospective, are then calculated (step 10) 218. As used herein, Potential Eligibility Scores (retrospective [PRES] and prospective [PPES]), are used to help depict "lost to follow-up" findings when methodology like "intent to treat" is utilized and are based on the "Study Time," i.e., the calendar (or clock) time of interest (e.g., the year 2110 Feb. 15 to Mar. 14, 1:00 A.M. to 1:15 A.M. on Apr. 3, 2001, etc.). Since some of the UOA-IDs may not be potentially eligible for the entire study time period, a score is given for each UOA-ID both prospectively and retrospectively. For example, the first individual in the above example "started" on January 1, which was also the first day of the study, a study which operationally ended Dec. 31, 2001. Accordingly, the individual's prospective Potential Eligibility Score is 12 Cohort months out of a possible 12 Cohort months (equivalent in this case to the 12 calendar months of the study). However, the individual's retrospective Potential Eligibility Score is based upon zero (0) retrospective Cohort months out of a possible 12 retrospective Cohort months (this score is 12 because any UOA-ID could have "started" on Dec. 31, 2001 and would therefore would be a maximum or potential 12 month period of time before onset) as there is no "potential" information available for the first individual prior to Jan. 1, 2001 (e.g. the individual's potential score is 12 divided by 12 and the individual's retrospective score is 0 divided by 12, which will default to zero by the algorithm). The second individual who "started" on Dec. 1, 2001 has one prospective Cohort month out of a possible 12 Cohort months of prospective eligibility so the individual's prospective Potential Eligibility Score is a function of 1 out of 12 (e.g. 1 divided by 12). The individual's retrospective Potential Eligibility Score is a function of 11 out of 12 (e.g. 11 divided by 12) as there is a potential of having 11 months of information on that individual (from Jan. 1, 2001 to Nov. 30, 2001) when the individual was not a member of the defined Population Retrospective data can be used in estimating "predictors" of becoming a member of a defined population, can be used to understand trends prior to becoming a member of a Population, etc. However, it is not necessary that UOA-IDs have both retrospective and prospective time segments. In fact, in two examples below all UOA-IDs have only prospective time segments. An example showing the potential eligibility scores are shown in Tables 7 and 8.

TABLE 7

| UOA-ID | Type | Start Time | Grouper | PTS + 1 | PTS + 2 | PTS + 3 | PTS + 4 | PTS + 5 | PTS + 6 |
|---|---|---|---|---|---|---|---|---|---|
| 123 | A | 15JAN2000 | X | 1.0 | 1.0 | 1.0 | 1.0 | 1.0 | 1.0 |
| 124 | C | 01APR2000 | X | 1.0 | 1.0 | 1.0 | 1.0 | 1.0 | 1.0 |

| UOA-ID | Type | Start Time | Grouper | PTS + 7 | PTS + 8 | PTS + 9 | PTS + 10 | PTS + 11 | PTS + 12 |
|---|---|---|---|---|---|---|---|---|---|
| 123 | A | 15JAN2000 | X | 1.0 | 1.0 | 1.0 | 1.0 | 1.0 | 0.5 |
| 124 | C | 01APR2000 | X | 1.0 | 1.0 | 1.0 | 0.0 | 0.0 | 0.0 |

| UOA-ID | Type | Start Time | Grouper | PTS − 6 | PTS − 5 | PTS − 4 | PTS − 3 | PTS − 2 | PTS − 1 |
|---|---|---|---|---|---|---|---|---|---|
| 123 | A | 15JAN2000 | X | 0.0 | 0.0 | 0.0 | 0.0 | 0.0 | 0.5 |
| 124 | C | 01APR2000 | X | 0.0 | 0.0 | 0.0 | 1.0 | 1.0 | 1.0 |

| UOA-ID | Type | Start Time | Grouper | PTS − 12 | PTS − 11 | PTS − 10 | PTS − 9 | PTS − 8 | PTS − 7 |
|---|---|---|---|---|---|---|---|---|---|
| 123 | A | 15JAN2000 | X | 0.0 | 0.0 | 0.0 | 0.0 | 0.0 | 0.0 |
| 124 | C | 01APR2000 | X | 0.0 | 0.0 | 0.0 | 0.0 | 0.0 | 0.0 |

TABLE 8

| UOA-ID | Type | Start Time | Grouper | PPES | PRES |
|---|---|---|---|---|---|
| 123 | A | 15JAN2000 | X | 11.5 | 0.5 |
| 124 | C | 01APR2000 | X | 9.0 | 3.0 |
| 123 | D | 10MAR2000 | Y | 9.33 | 2.66 |

Key: PPES = Potential Prospective Eligibility Score (sum of PTS+ values), PRES = Potential Retrospective Eligibility Score (sum of PTS values)

As used herein, the "Actual Eligibility Score" is the proportion of each time segment that the UOA-ID was eligible to be a member of a specific Population. For example, if the time segment comprises 30 days and the UOA-ID was eligible to be in the Population for 15 days of that time segment, the Actual Eligibility Score would be 0.5. If the UOA-ID were eligible to be in the Population for the entire 30 days of a time segment, the Actual Eligibility Score would be 1.0. It should be understood that if there were no information for the UOA-ID for a particular time segment, the Actual Eligibility Score would be assigned the value of "missing." As will be seen later herein, by assigning the value of "missing" takes the UOA-ID out of the study for that particular time segment thereby eliminating any inaccurate biasing of the data. An example showing the Actual Eligibility Scores are shown in Tables 9 and 10.

TABLE 9

| | Input | |
|---|---|---|
| UOA-ID | Eligibility Start | Eligibility End |
| 123 | 01JAN1999 | 31MAR2000 |
| 123 | 01APR2000 | 31DEC2000 |
| 124 | 01APR2000 | 01JUN2000 |

TABLE 10

| UOA-ID | Type | Start Time | Grouper | TS − 2 | TS − 1 | TS + 1 | TS + 2 |
|---|---|---|---|---|---|---|---|
| 123 | A | 15JAN2000 | X | . | 0.5 | 1.0 | 1.0 |
| 124 | C | 01APR2000 | X | . | . | 1.0 | 1.0 |

Using the Actual Eligibility Score, as illustrated in Tables 11, 12 and 13, the AdjVAR Value is adjusted again with respect to eligibility by performing the appropriate mathematical function for each time segment (step 10) 218 to generate an Eligible Adjusted Variable Value ("EAV") for the time segment. It should be understood that the EAV, as used herein, is expressed by the same units as used for the VAR Value. Further, for any UOA-ID that is eligible (actual) for any given time segment, if there is no VAR Value ("missing") the UOA-ID would be assigned a value of "0." Thus, EAV may be, but are not limited to, a quantity count, dollar value, number of products, and number of events, etc.

TABLE 11

| | Input (AdjVAR per TS FROM STEP 9) | | | | | | |
|---|---|---|---|---|---|---|---|
| UOA-ID | Type | Start Time | Grouper | TS − 2 | TS − 1 | TS + 1 | TS + 2 |
| 123 | A | 15JAN2000 | X | . | . | 100 | 5100 |
| 124 | C | 01APR2000 | X | . | . | 515 | . |

TABLE 12

| | Input (Actual Eligibility per TS FROM STEP 10) | | | | | | |
|---|---|---|---|---|---|---|---|
| UOA-ID | Type | Start Time | Grouper | TS − 2 | TS − 1 | TS + 1 | TS + 2 |
| 123 | A | 15JAN2000 | X | . | . | 0.5 | 1.0 |
| 124 | C | 01APR2000 | X | . | . | 1.0 | 1.0 |

TABLE 13

| | Output: | | | | | | |
|---|---|---|---|---|---|---|---|
| UOA-ID | Type | Start Time | Grouper | EAV − 2 | EAV − 1 | EAV + 1 | EAV + 2 |
| 123 | A | 15JAN2000 | X | . | . | 200 | 5100 |
| 124 | C | 01APR2000 | X | . | . | 515 | 0 |

Key: EAV = Eligiblity adjusted AdjVAR

After the Software has calculated the EAV the software operates (step 12) 222 to prepare an aggregate or Summary Metric for all the UOA-ID's in a time segment. For example, for a given time segment, the average, medium, etc. EAV may be calculated. The Summary Metric is then used, together with the various inputs and derived parameters, to calculate an Output Expression. It should be understood to those skilled in the art that the Output Expression can be in the form of a display, such as, but not limited to, a video, printed matter, projected image, or a recorded display, which can then be used for analyzing and evaluating resource allocation.

As used herein, the Output Expression is any representation that can show a relationship between one or more of the Summary Metrics, and the inputs and derived parameters and may be generated using various techniques. In a preferred embodiment of the invention, the Output Expression is in the form of a graphic representation, table or a chart.

In order to better illustrate the method and system for analyzing resource allocation, the following examples are provided:

EXAMPLE 1

Health Care

The present invention provides a method and a system for implementing the method of identifying effective resource allocation in the health care industry. As used in this example, effective resource allocation includes evaluating where to allocate current resources for the purpose of obtaining a desired outcome, such as reducing excessive costs due to overutilization or resources, as well as assessing the impact that such the resources had on the resulting outcome. Unfortunately, until now the current metric systems typically used in the health care industry operate to compute costs over large time periods (e.g. a calendar year) in defined populations and fail to account for changes in cost patterns in certain patient Populations within these large time segments.

The transaction of this example is initiated by the interaction between a health care provider and a patient where the Type (e.g. diagnosis or product) is "purchased" on a specific date and/or time (CCT). Coupled with eligibility to experience a transaction, the method and system for utilizing the method of the present invention transforms these data into Cohort time trends of utilization (e.g. cost) per Type. These trends are then used to 1) better understand current trends in Cohort Time, and 2) to better estimate resource allocation to meet specific goals of improving utilization over Cohort Time or CCT.

For this example, the UOAs are specific patients within a defined Population and the UOA-ID is a unique individual who meets the criteria for a defined Population based on Type (or Types). Type shall be a diagnosis, drug, code (based for example on ICD9), etc. The CCT shall be the calendar or clock time of the transaction. VAR Value shall be the amount of the transaction or some numeric value.

Table 14 illustrates the method of the present invention in accordance with example 1.

TABLE 14

| STEPS | Health Care Example |
|---|---|
| 1 | Identify each UOA (patients within a defined Population), UOA-ID (a specific patient), Type (a diagnosis, drug, code, etc.), CCT (time of the transaction), VAR Value (amount of transaction) |

TABLE 14-continued

| STEPS | Health Care Example |
|---|---|
| 2 | Group each UOA-ID into appropriate Groupers and store into separate "K" files. The "Grouper" takes many "Types" (e.g. diagnoses) codes and creates a new "Grouper" variable." Separate into data set per each Grouper. |
| 3 | Organize each UOA-ID within each Grouper "K" file by succeessing CCT. |
| 4 | Select the earliest Start Time per UOA-ID |
| 5 | Input length of time segment period(s). For example, 30 days. |
| 6 | Form time segments, retrospective and prospective, based on the Start Time. The time segments are based upon time before and after the Start Time in 30 day increments. |
| 7 | Adjust and standardize each VAR Value to create AdjVAR Values. In this example VAR Value (e.g., $) is influenced by calendar time (e.g. inflation). |
| 8 | Sort and place AdjVAR Values into appropriate time segments based upon a match of the time of the AdjVAR Value transaction. |
| 9 | Repeat steps 1-8 for each UOA-ID |
| 10 | Calculate an Eligibility Score (potential and actual) prospective and retrospective for each UOA-ID. Based upon calendar or clock time of study each UOA-ID receives a potential score. Based upon the actual eligibility during each time segment each UOA-ID receives an Actual Eligibility Score per time segment |
| 11 | Calculate the Adjusted variable Value (EAV) for each time segment. Mathematical Operation (situation specific). In this example the AdjVAR is divided by the Actual Eligibility Score to generate an EAV. The assumption that was made in this example is that if the UOA-ID had been eligible it would have had a similar AdjVAR Value across the entire time period. If proportion eligibility was 0.5 and AdjVAR Value was $100, then the EAV would be $200.00. The assumption is that if an UOA-ID had been eligible the entire month one needs to know the expected value. The Potential Eligibility score should be merged with the EAV for proper interpretation of Output Expression |
| 12 | Generate an Output Expression. From this step, the "average" (or other summary metric) of one defined Population can be trended per time segment (30 days) and compared to the trend of the percent of other populations (or sub-sets per Population based upon other Types and/or other variables, e.g. age, sex, etc). A dichotomous variable (DV) is calculated from "threshold value" (e.g. $99^{th}$ percentile of costs) and the Population is trended over time segment based upon the percent of the Population above the threshold |

The term "Health care" has a wide range of meanings. It should be understood that method and system for performing the method of the present invention could be used for different purposes and different functions. For example, it can be used by the "payers" (Health care insurance, employer, government, etc.), "providers" (e.g. hospitals, physicians, nursing homes, etc.) disease management functions, utilization management, case management, concurrent review, actuarial pricing, health economics, and the evaluation of "technology" including pharmaceuticals and durable medical goods and devices ( i.e., "technology assessment")

EXAMPLE 2

Marketing

In this example, the method and the system for performing the method of the present invention is utilized for use in the marketing industry. Often in the advertising industry the effectiveness of an advertisement is related to the amount of time it is viewed. This is particularly true in marketing using the Internet or over mass media, such as radio or television, where advertising time is relatively expensive. It is therefore important to optimize the average viewing time. Accordingly, the advertiser needs to be able to evaluate and analyze the trend over time and to determine how much to spend and how to improve viewing time.

In accordance with this example, the method and the system of the present invention uses an individual view of an individual advertisement (Type) and transforms this into a trend of viewship over Cohort Time per Type (or Grouper) in the population. These trends can be used to understand the current time segment "view" per advertisement (comparisons to other advertisements are possible as are comparisons by web site if used in Internet marketing, etc.) and to better analyze and evaluate resource allocation to meet specific goals or improving viewship.

For this example, the UOA is an individual who viewed an advertisement (i.e. based on Type, which in this example is a code of a specific advertisement). The UOA-ID can be unique or not unique (a known individual or not). The Start Time for each UOA-ID shall be the CCT that the UOA-ID began viewing the advertisement. For the Internet the CCT can be when the UOA-ID enters a web page. The end time for each UOA-ID shall be the calendar/clock time when the UOA-ID stopped viewing the advertisement. For the Internet this can be when the UOA-ID leaves a web page. The VAR Value for each time segment can vary for each time segment. For example, if three time segments are selected, the VAR Values can have three different values, such as $1.00, $2.00, and $3.00. This is an example of VAR Values being rather than a variable that varies per UOA-ID, as illustrated in Example 1.

Table 15 illustrates the method of the present invention in accordance with example 2.

TABLE 15

| STEPS | DESCRIPTION |
|---|---|
| 1 | Identify UOA (individual who viewed advertisement), UOA-ID (a known or unknown individual), Type (individual advertisement), CCT (time viewed), VAR Value (value of viewing) |
| 2 | Group each UOA-ID into appropriate Groupers and place into separate Grouper "K" files. The "Grouper" is equivalent to the "Type" here, seperate each UOA-ID into one or more data sets per each "Grouper." |
| 3 | Organize each UOA-ID within each Grouper "K" file by succeessing CCT. |
| 4 | Select the earliest Start Time per UOA-ID. In this case all Start Times are valid as the UOA-ID is defined as an individual viewing of the Type. |
| 5 | Input length of time segment period(s) |
| 6 | Form time segments, retrospective and prospective, based on Start Date The time segments are based upon time from Start Time. |
| 7 | Adjust and standardize each VAR Value to create AdjVAR Values (e.g., When VAR Value is $ that are influenced by calendar time inflation) |
| 8 | Sort and place AdjVAR Value for each UOA-ID into the appropriate time segment (TS). |
| 9 | Repeat steps 1-8 for each UOA-ID |
| 10 | Calculate an Eligibility Score (potential & actual) prospective only (in this example there is no retrospective eligibility score) for each UOA-ID. Potential eligibility is based on whether the viewer at any specific time view, e.g. based upon hours opened, machine plugged in, etc. In all |

TABLE 15-continued

| STEPS | DESCRIPTION |
|---|---|
| | likelihood, each UOA-ID viewing will have full potential. In Actual Eligibility missing, 0, 1, based upon actual "viewing" per UOA-ID. In this case there are no "partial" eligibility scores, (i.e. "Viewing" was made or not made). |
| 11 | Calculate the Adjusted Variable Value (EAV) for each time segment. Mathematical Operation (situation specific). Option 1: In this example the AdjVAR Value is multiplied by the eligibility value to generate the EAV. For example, if proportion viewed (i.e. Actual Eligibility) of the advertisement was 0.5 and AdjVAR Value was $1.00, then the EAV would be $.50. The actual viewing of the advertisement was ½ the total time. Option 2: If the payment occurred with any viewship one would recode Actual Eligibility with values of >0 to 1.0 and multiply. Option 3: if the payment occurred with only full viewship per time segment, anything less than 1 would be coded as 0. |
| 12 | Generate an Output Expression. Example: Display trends in viewship over time by product. |

EXAMPLE 3

Legal Profession, Trademark Evaluation

Trademarks or trade dress are valuable business assets and can comprise anything that is adopted and used to identify the source or origin of goods and which is capable of distinguishing them from goods emanating from a competitor. A trademark however, is not generally given legal protection if the mark is deemed merely descriptive or deceptively misdescriptive, or is primarily geographically descriptive or if it is primarily merely a surname unless proof of distinctiveness can be shown. One method of showing distinctiveness is la use of a survey of consumer association of a mark with a product. While courts have found such surreys persuasive in determining distinctiveness, such surveys are often challenged by competing studies. Surveys have also been used in trademark infringement litigation on issues of whether or not two marks are likely to cause confusion or whether or not a mark has become generic. In addition to determining whether or not a mark can be given legal protection or likely to cause confusion, survey results may also be used to evaluate the strength of a mark. This may be particularly important for use in selecting a mark or for evaluating a potential infringement action. Accordingly, those using such surveys are continuously looking at ways to better analyze and evaluate consumer reactions or their perceptions to trademarks or their perception of a single trademark.

In accordance with this example, the method and system of the present invention is used to estimate the extent of injury caused by trademark infringement and whether or not litigation should be pursued. The two products (The trademark owner's product and the accused infringing product) thought to have a similar look are being evaluated to determine if consumers would discern the differences in their appearance. Preferably, for this study the two products are placed together, such as side-by-side, in a retail outlet and a monitoring device is utilized to determine the "length of viewing time" (i.e. start of viewing and end of viewing resulting in a product selection by the customer).

For this example, the UOA is an individual who viewed the products (i.e. based on Type). The UOA-ID of the individual is or is not unique. The Type is the code for a specific product.

The Start Time is the time, which "viewing" started, and the VAR Value is the value of the revenue to the trademark owner.

Table 16 illustrates the method of the present invention in accordance with example 3.

TABLE 16

| STEPS | DESCRIPTION |
|---|---|
| 1 | Identify UOA (individual who viewed the products), UOA-ID (specific individual, known or unknown), TYPE (code for the specific product), CCT (time product was viewed), VAR Value (value of the revenue to the trademark owner). |
| 2 | Group each UOA-ID into appropriate Grouper and place into separate Grouper "K" files. The "Grouper" may be equivalent to the Type (in this example Grouper and Type are equivalent). |
| 3 | Organize each UOA-ID within each Grouper "K" file by succeessing CCT. Separate each UOA-ID into >=1 data sets per each "Grouper." Per UOA-ID sorts by CCT. |
| 4 | Identify Start Time. Select the earliest CCT per UOA-ID. In this case all Start Times are valid as the UOA-ID is defined as an individual viewing of the Type. |
| 5 | Identify the time segment. In the example, it was 1 second. |
| 6 | Form time segments, retrospective and prospective, based on Start Date. The time segments are based upon time from Start Time and will only be prospective |
| 7 | Adjust and standardize each VAR Value to create AdjVAR Values. (e.g., When VAR Value is $ that are influenced by calendar time inflation). |
| 8 | Sort and place AdjVAR Value in the appropriate time segment based upon time of AdjVAR transaction. |
| 9 | Repeat steps 1-8 for each UOA-ID |
| 10 | Calculate an Eligibility Score (potential & actual) prospective and retrospective for each UOA-ID. Potential Eligibility is based on whether the UOA-ID ("viewer") at any specific time view, e.g. based upon hours opened, machine plugged in, etc. In all likelihood, each UOA-ID viewing will have full potential. In Actual Eligibility missing, 0, 1, based upon actual "selection" per UOA-ID. In this case there are no "partial" eligibility scores, (i.e. The selection was made or not made). |
| 11 | Calculate the Eligibility Adjusted AdjVAR Value (EAV) for each time segment. Mathematical Operation (situation specific). In this case the VAR Value is multiplied by eligibility value to generate an EAV. |
| 12 | Generate an Output Expression(s) Display trends in "percent selected" over Cohort time segments without regard to stratifying variable (Product). Calculated trend of population "selecting" product A (trademark owners product) vs. Product B (infringing product) per time segment, The addition of other variables showing characteristics of UOA-ID (e.g. age, income level, region, etc) will allow the trends to be stratified by these variables to determine prevalence of each customer type. Calculate outcome "cash value" and available resources that can be allocated to acheive outcome. |

The percentage of the Population "selecting" product A will be trended per time segment (second) and compared to the trend of the percentage of the Population "selecting" product B. The addition of other variables showing characteristics of UOA-ID (e.g. age, income level, region, etc) will allow the trends to be stratified by these variables to determine prevalence of each customer type.

In order to illustrate the various Output Expressions that can be generated using the method and the system of the present invention, FIGS. 3 through 6 and associated descriptions are used and should not be construed to define or bound the present invention. It should be understood that the values shown in Tables 17-24 are for illustrative purposes only.

Figure 4:
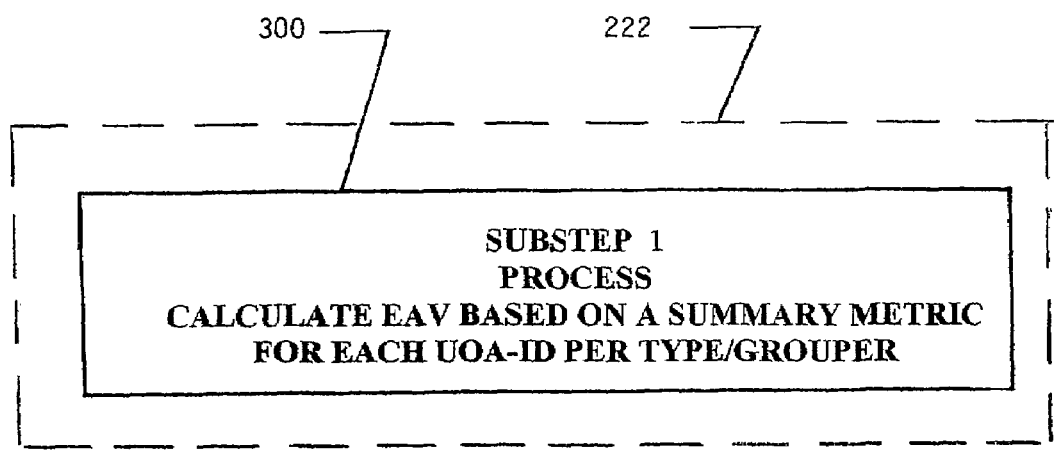
FIG. 4 is a flow diagram illustrating the various functional steps for generating a first typical Output Expression showing an EAV trend based on a selected summary metric.

Referring to FIGS. 3 and 4 is a flow diagram illustrating in more detail step 12 222 of the method of generating a first typical Output Expression. In this example, as shown in Table 4, the Output Expression generated in substep 1 300 is an EAV trend that is based on a selected summary metric (e.g. mean, median, average, etc.) for all UOA-IDs per Type or Grouper for each time segment. As used herein, the Index Time Segment is the initial or "Start Time" as previously defined and only prospective time segments are shown.

TABLE 17

| Time Segment (TS) | EAV Summary Metric |
|---|---|
| TS + 1 (Index) | $2,656.76 |
| TS + 2 | $ 525.81 |
| TS + 3 | $ 548.19 |
| TS + 4 | $ 533.17 |
| TS + 5 | $ 416.15 |
| TS + 6 | $ 304.30 |

Figure 5:
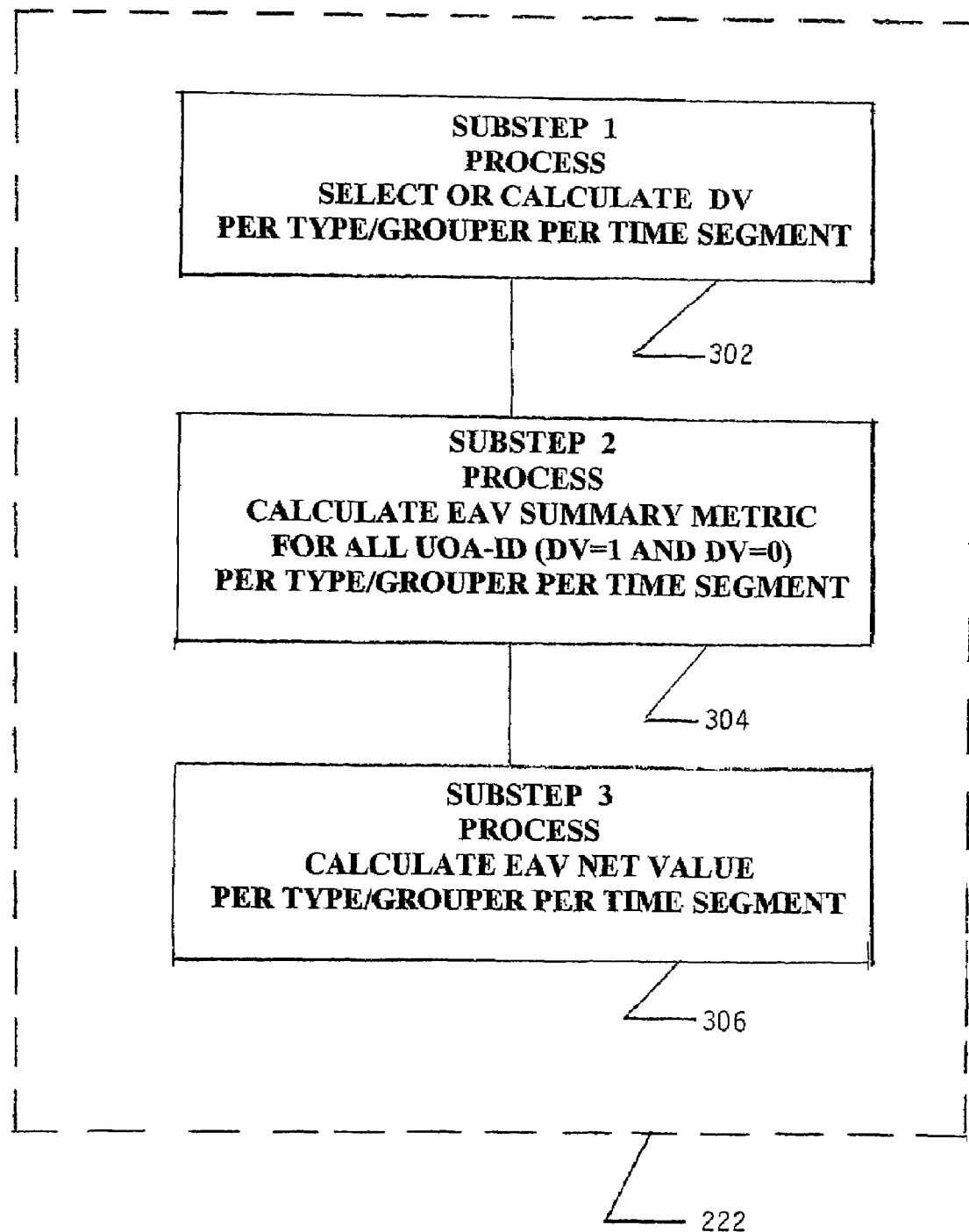
FIG. 5 is a flow diagram illustrating the various functional steps for generating another typical Output Expression showing an EAV Net Value Summary Metric based on a dichotomous variable.

Referring to FIGS. 3 and 5 is a flow diagram illustrating in more detail step 12 222 of the method of generating a typical Output Expression. Another typical Output Expression that can be generated by the method and system of the present invention is shown and comprises an EAV summary metric trend in dichotomous variable form (i.e. a variable with values of "0" and "1") per Type/Grouper per time segment. Depending on the particular study, the DV can be either a "1" or a "0." For example in the marketing example (previous Example 2) when the UOA-ID is viewing, he or she would be given an eligibility value of "1" during that time segment and when not viewing the UOA-ID would be given an eligibility value of "0" during that time segment. For the trademark evaluation example (previous Example 3) the UOA-ID would be given an eligibility value of "0" for the time segment he or she did not select a product and a "1" for the time segment he or she did select the product. The DV can also be calculated based on a selected or calculated threshold EAV value (such as in the previous health care Example 1) whereby the EAV is placed, into dichotomous variable form by determining when the VAR Value for a UOA-ID exceeds a specified threshold value, if it does the UOA-ID would be given a DV equal to "1", if not the DV would be "0". As used herein, the "Threshold value" is an arbitrary cost provided by the user. This cost could be but not limited to, the amount currently being spent in a program, target costs, or some other value of importance to the user.

As shown in FIG. 5 and illustrated in Table 18, step 12 222 of the method of the present invention includes substep 1 302 of selecting or calculating a DV per Type/Grouper per time segment. For example, as shown in Table 5, for TS+1 (Index), 37.6% of UOA-Ids received a DV equal to "1."

TABLE 18

| Time Segment (TS) | Percent Dichotomous Variable [DV = 1/ (DV = 1 + DV = 0)*100] |
|---|---|
| TS + 1 (Index) | 37.6 |
| TS + 2 | 8.4 |
| TS + 3 | 8.1 |
| TS + 4 | 6.2 |
| TS + 5 | 6.6 |
| TS + 6 | 3.1 |

After completing substep 1 302, as illustrated in Table 19, the EAV summary metric is calculated using Tables 4 and 5, substep 2 304, for all UOD-IDs with a DV of "1" and for a DV of "0" per Type/Grouper per time segment. For example, for TS+1 (Index) 37.6% UOA-Ids had an EAV Summary Metric of $6,953.00 and 62.4% UOA-Ids have an EAV Summary Metric of $68.00. It should be understood that Table 17 is essentially a weighted average of the values reflected in Tables 18 and 19.

TABLE 19

| Time Segment (TS) | EAV Summary Metric (Where DV = 1) | EAV Summary Metric (Where DV = 0) |
|---|---|---|
| TS + 1 (Index) | $6,953 | $68 |
| TS + 2 | 5,649 | 56 |
| TS + 3 | 6,087 | 60 |
| TS + 4 | 7,480 | 74 |
| TS + 5 | 5,527 | 55 |
| TS + 6 | 7,503 | 74 |

The EAV Net Value per Type/Grouper per Time Segment is then calculated, substep 3 306. As used herein, as illustrated in Table 20, the EAV Net Value is the difference in EAV between a DV equal to "1" to the DV equal to "0", or vice versa.

TABLE 20

| Time Segment (TS) | EAV Net Value (DV = 1 − DV = 0) |
|---|---|
| TS + 1 (Index) | $6,885 |
| TS + 2 | 5,593 |
| TS + 3 | 6,027 |
| TS + 4 | 7,406 |
| TS + 5 | 5,472 |
| TS + 6 | 7,429 |

Figure 6:
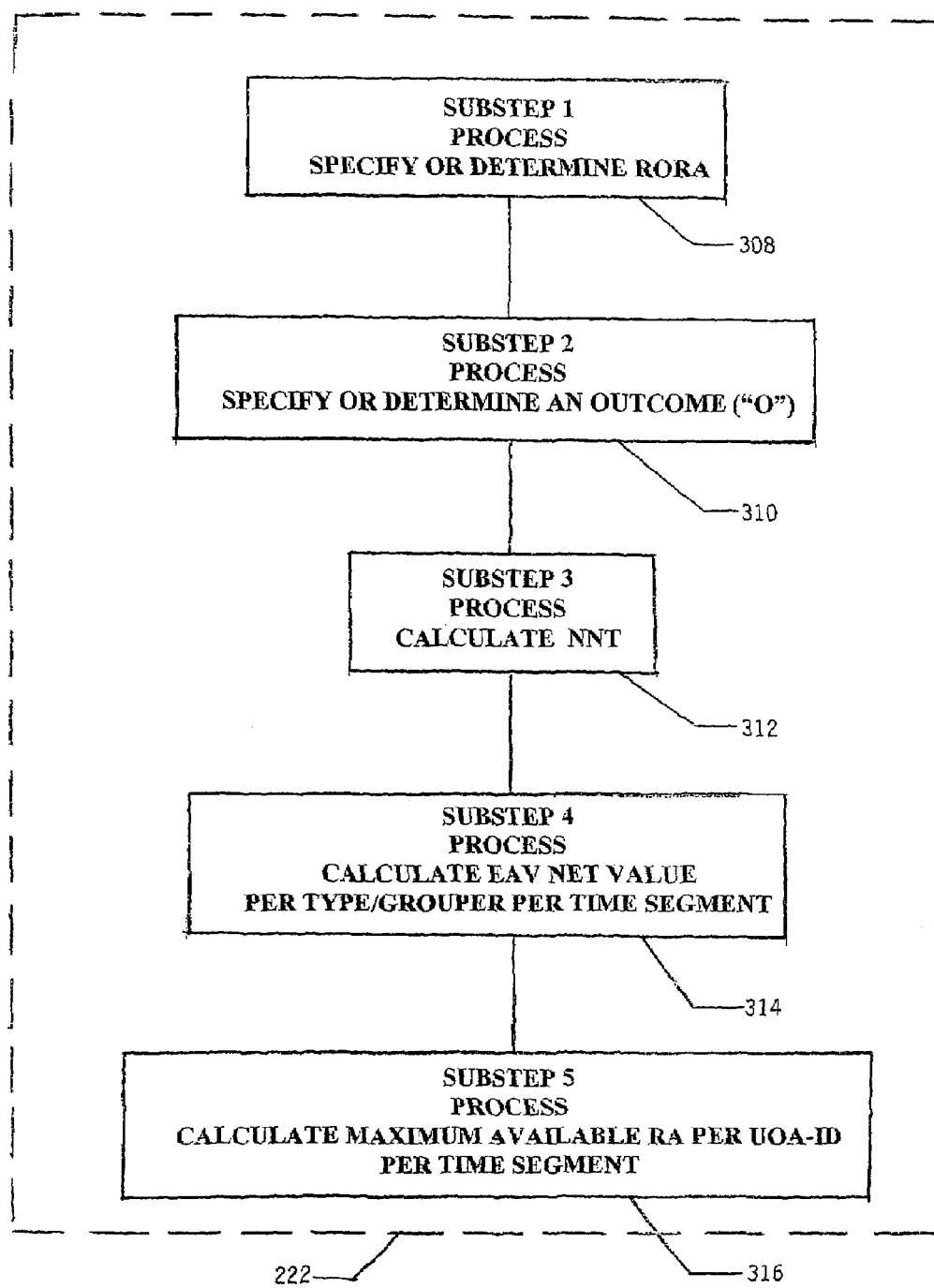
FIG. 6 is a flow diagram illustrating the various functional steps for generating another typical Output Expression showing available Resource Allocation.

Referring to FIGS. 3 and 6 is a flow diagram illustrating in more detail step 12 222 of the method of generating a typical Output Expression. Another typical Output Expression that can be generated by the method and system of the present invention comprises a showing of the maximum available resource allocation ("RA") per time segment.

As illustrated in Table 21, step 12 222 of the method of the present invention includes substep 1 308 of specifying or determining a return on resource allocation ("RORA"). segment. In this specific example, the RORA is selected to be 1.0 that represents the RORA break-even point.

TABLE 21

| Time Segment (TS) | Return on Resource Allocation (RORA) |
|---|---|
| TS + 1 (Index) | 1.0 |
| TS + 2 | 1.0 |
| TS + 3 | 1.0 |
| TS + 4 | 1.0 |
| TS + 5 | 1.0 |
| TS + 6 | 1.0 |

After completing substep 1 308, an Outcome ("O"), as illustrated in Table 21, is specified by the user substep 2 310. As used herein the "Outcome" is the expected change in percentage of DV equal to "1" per time segment (For example, between "old" and "new" EAVs per time segment). As used in this case, a change of 10% in the percent of the DV (as shown in Table 18) is desired. In TS+1(Index), a 10% change of 37.6% would be 3.76 percentage points or an expected 33.84 percent DV (37.6-3.76=33.84).

TABLE 22

| Time Segment (TS) | Expected Change |
|---|---|
| TS + 1 (Index) | 10% |
| TS + 2 | 10% |
| TS + 3 | 10% |
| TS + 4 | 10% |
| TS + 5 | 10% |
| TS + 6 | 10% |

The number needed to target ("NNT") to impact one UOA-ID per time segment is then calculated in substep 3 312. For example, for a total Population being equal to 100%, the percentage of Population with a DV equals to "1" is determined. The user can then specify the desired Outcome ("O"), such as 10%, and the NNT is calculated, as illustrated in Table 23, by dividing the total Population by the percentage of the population where the DV is equal to "1" and further dividing by the desired Outcome (NNT=(Total Population/Percentage of Population With a DV equal to "1")/Outcome).

TABLE 23

| Time Segment (TS) | Formula (substep 3) | NNT (Number Needed to Treat)* |
|---|---|---|
| TS + 1 (index) | (100/37.6)/10 | 27 |
| TS + 2 | (100/8.4)/10 | 119 |
| TS + 3 | (100/8.1)/10 | 123 |
| TS + 4 | (100/6.2)/10 | 161 |
| TS + 5 | (100/6.6)/10 | 152 |
| TS + 6 | (100/3.1)/10 | 323 |

*NNT is rounded to an integer in this example.

The EAV Net Value is then calculated in substep 4 314 and is then used to calculate the maximum available resource allocation ("RA") per UOA-ID per time segment substep 5 316. Available resource allocation ("RA") is calculated, as illustrated in Table 25, by dividing the EAV Net Value by the number needed to target ("NNT") which was previously calculated in substep 3, 310 (RA=O/RORA).

TABLE 24

| Time Segment (TS) | Formula* | RA |
|---|---|---|
| TS + 1 (index) | ($6,885/27)/1.0 | $255 |
| TS + 2 | ($5,593/119)/1.0 | $ 47 |
| TS + 3 | ($6,027/123)/1.0 | $ 49 |
| TS + 4 | ($7,406/161)/1.0 | $ 46 |
| TS + 5 | ($5,472/152)/1.0 | $ 36 |
| TS + 6 | ($7,429/323)/1.0 | $ 23 |

*(EAV Net Value/NNT)/RORA = RA. The integer value of NNT from Table 23 was used here
**NNT is based on the rounded value as an integer.

It should now be apparent that with all of the various Output Expressions, the Cohort Time trend calculated per group (or sub-group) can be compared to other groups (or sub-groups). This can be based on Type or another variable and can be used to determine Resource Allocation ("RA"), Output ("O"), and Return on Resource Allocation ("RORA") per these sub-groups/Types. It should also now be apparent to those skilled in the art that as shown from the above description the RA, RORA, and the Output are related mathematically. Accordingly, where two of such values are known, the third can be easily calculated using simple algebra Thus the method can be used to calculate estimates such as "return on investment" (RORA in the terminology used here) when the outcome and the resources allocated are known. Moreover, if RORA and RA are known, the outcome can be estimated. The latter is useful when comparing the impact of a certain resource allocation decision on one population, compared to another resource allocation decision on another comparable (e.g., both selected by randomization) Population.

This grouping stratification can be based on variables (including Type) that are derived from inputted variables in the Index Time segment only, other time segment only, or all time segments. For example:

into CCT for financial budgeting and reporting. This can be accomplished by inclusion of the "Start Time" CCT into data set per UOA-ID by Type/Grouper. That is, using the resources allocation estimates per cohort time segment, these time segment specific estimates can be place back into CCT to estimate resources allocated per CCT time segment. This is accomplished by maintaining the start CCT per UOA-ID in the set of information See Table 25 for example the simple method of transforming Cohort Time values for budgeting per calendar time.

TABLE 25

| Distribution per Calendar Time Segment (equal in duration to Cohort TS) | DV = 1 (expected percentage) | DV = 0 (expected percentage) | Total (expected percentage) | RA ESTIMATES (per UOA-ID)* |
|---|---|---|---|---|
| TS + 1 (index TS) | 37.6% | 62.4% | 100.0 | $255 |
| TS + 2 | 8.4 | 91.6 | 100.0 | $ 47 |
| TS + 3 | 8.1 | 91.9 | 100.0 | $ 49 |
| TS + 4 | 6.2 | 93.8 | 100.0 | $ 46 |
| TS + 5 | 6.6 | 93.4 | 100.0 | $ 36 |
| TS + 6 | 3.1 | 96.9 | 100.0 | $ 23 |
| Column Sum/ Number of Cohort Time Segment | 69.99%/6 | 529.99%/6 | 600/6 | $456/6 |
| Budget Estimates (Column Average) | 11.67% | 88.33% | 100.0% | $ 76 |

Key to table: *Resource Allocation (RA) Estimates (where Outcome expectation = 10% and Return on Resource Allocation = 1.0) The calculations are based on a equal weighting of UOA-ID per Cohort time segment. Thus (100/6 or 16.66%) of the total Population during any calendar time segment is in any of the six Cohort Time segments. A simple weighting system can be applied to alter the column average.

1) A "count" (the number of times an UOA-ID is above the threshold). For example if there were four time segments, any UOA-ID could have the "count" value of 0, 1, 2, 3, or 4) can be used. This "count" variable can become a stratifying variable to determine RORA, RA, or O per time segment.
2) The trend of the UOA-IDs above some threshold value in the Index Month can be calculated to determine the percentage of this sub-population (a) above the threshold in other months (prospective or retrospective) and/or (b) below the threshold in other months.
3) The trend of the UOA-IDs that are not above some threshold in the Index Month can be calculated to determine the percentage of this sub-population that (a) continue at or below the threshold in other months or (b) that change status to the group above the threshold in other months.
4) The trends of No. 2 and No. 3 can be calculated beginning the analysis in a month other than the Index Month (this can be valuable when the data is not immediately available and potential actions to change trends will only occur in time segments other than the Index Time Segment).
5) Using an additional variable (e.g., where an UOA-ID has evidence of another "Type" in either the Index Month or other months). Subdivide the Population by those with this additional "Type" and those without this additional "Type" and calculate trends and RA, O, and RORA as needed.
6) Using any additional variable (other than Type) that is included in some set of information (that can be linked to a UOA-ID) any time segment, this can be fixed (e.g. sex) or variable (e.g., sales per month), and stratify by this variable, calculating trends, and RA, O, and RORA.

It should be flow be apparent to those skilled in the art that these Cohort Time calculations can be easily translated back Further, it should also now be apparent to those skilled in the art that each RA, O, or RORA can be summarized over all time segments to determine an overall RA, O, or RORA (e.g. using averages or summations).

It should also now be apparent to those skilled in the art that the method and the system of the present invention transforms economic and eligibility information produced over calendar/clock time (CCT) per a unique unit of analysis (e.g. UOA-ID) that meets the criteria for inclusion into a specific Population (Type or Grouper) into information organized by Cohort Time and summarized across all UOA-IDs that are part of the same Population. This is accomplished by determining the time segment and its duration, the population in which the UOA-ID is entered (based on Type), the value of some economic variable (VAR Value), and the potential and eligibility of the UOA-ID per time segment. As previously described, the Population is based on a criterion or a set of criteria (Type) that a UOA-ID must meet to be a member. The time/date at which the UOA-ID meets the Type is the "Start Time." The VAR Value is an economic variable that can be specified or calculated and can be fixed or variable per each time segment or fixed or variable per UOA-ID. The potential eligibility score is based on the time of the study and determines per UCA-ID which time segments (both prospective and retrospective) have the potential to have VAR Values in them. This a function of Start Time in which each UOA-ID entered the Population and the range of CCT of the study time. The actual eligibility score is based upon the Start Time in which the UOA-ID entered the Population and is calculated based on the UOA-ID. A "missing" value in VAR Value during a time segment can mean either the UOA-ID was eligible and had no VAR Value or that the UOA-ID was not potentially eligible and the UOA-ID had no VAR Value. The VAR Value and the eligibility scores can then be merged to calculate an EAV. The EAVs can be summarized across all the UOA-IDs to enable one to estimate resources that can be allocated per UOA-ID per Cohort time segment to reach a defined outcome based on a defined return on resource allocation estimate.

It has been found and should be understood to those skilled in the art that the method and the system for performing the method of the present invention has application across a wide range of businesses and industries including, but not limited to, health care industries, insurance industries, manufacturing industries, the marketing and advertising industries, travel industries, and retail industries. For example, the method of the present invention can be easily translated for warranty applications, actuarial applications, insurance applications, marketing and advertising applications, frequent use program applications, shopping card applications, trademark/trade dress/product design evaluation applications, infringement applications, etc.

Accordingly, the present invention is a method and system to qualitatively analyze cost reduction programs and for analyzing data for allocating resources to best serves a business' goals. The method and apparatus transforms this information into usable estimates of resource allocation needed to achieve specified outcomes.

Although the foregoing invention has been described in some detail for purposes of clarity of understandings, it will be apparent that certain changes and modifications may be practiced within the scope of the appended claims. Furthermore, it should be noted that there are alternative ways of implementing both the method and system for implementing the method of the present invention. Accordingly, the present embodiments are to be considered as illustrative and not restrictive, and the invention is not to be limited to the details given herein, but may be modified within the scope and equivalents of the appended claims.

I claim:

1. A system for performing a study of analyzing resource allocation comprising:
   system software; and
   a central processing unit for implementing said system software, wherein said system software operates to perform the method having the steps of:
   identifying at least one criterion for inclusion into a specific population;
   identifying sets of information wherein each set of information includes a particular Individual Unit of Analysis entity involved in the study (UOA-ID), a Calendar Clock date/time (CCT), and a Variable Value (VAR Value);
   grouping each UOA-ID from said sets of information into the appropriate said specific population (Type);
   identifying a Start Time wherein each UOA-ID has met said at least one criterion;
   forming at least one prospective or retrospective Cohort time segment for each UOA-ID based on their Start Time;
   placing each UOA-ID into the appropriate said Cohort time segment;
   calculating an eligibility score for each UOA-ID for each said Cohort time segment;
   calculating an Eligible Adjusted Variable Value for each UOA-ID for each said Cohort time segment; and
   generating at least one Output Expression showing at least one trend of a particular population, said at least one trend expressed in at least one of said Cohort time segment and wherein said at least one Output Expression is based on said Eligible Adjusted Variable Value and said UOA-ID for each said Cohort time Segment;
   and wherein the system further includes analyzing and evaluating a resource allocation utilizing the generated said at least one Output Expression.

2. The system of claim 1 wherein said method further comprising the step of transforming said at least one Output Expression from being expressed in Cohort time segments to being expressed in CCT segments.

3. The system of claim 1 wherein said at least one trend relates to the viewing time of advertising.

4. The system of claim 1 wherein said at least one trend relates to the extent of injury caused by trademark infringement.

5. The system of claim 1 wherein said at least one trend relates to the health care industry.

6. The system of claim 1 wherein said method further comprising the step of calculating an Eligible Adjusted Variable Value (EAV) based on a summary metric for each UOA-ID per Type to generated said at least one said Output Expression.

7. The system of claim 1 wherein said method further comprising the steps of:
   determining a Dichotomous Variable (DV) per Type time segment;
   calculating an Eligible Adjusted Variable Value (EAV) summary metric for all UOA-IDs per Type per time segment; and
   calculating an EAV Net Value per Type per time segment to generate at least one Output Expression.

8. The system of claim 1 wherein said method further comprising the steps of:
   determining a Return On Resource Allocation(RORA);
   determining an Outcome;
   calculating a Number Needed to Target (NNT);
   calculating an Eligible Adjusted Variable Value (EAV) Net Value per Type per time segment; and
   calculating the maximum available Resource Allocation (RA) per UOA-ID per time segment to generate said at least one Output Expression.

9. The system of claim 1 wherein said method further comprising the steps of:
   determining a Resource Allocation (RA);
   determining an Outcome;
   calculating a Number Needed To Target (NNT);
   calculating an Eligible Adjusted Variable Value (EAV) Net Value per Type per time segment; and
   calculating the Return On Resource Allocation (RORA) per UOA-ID per time segment to generate said at least one Output Expression.

10. The system of claim 1 wherein said method further comprising the steps of:
    determining a Return On Resource Allocation(RORA);
    determining a Resource Allocation (RA);
    calculating a Number Needed To Target (NNT);
    calculating an Eligible Adjusted Variable Value (EAV) Net Value per Type per time segment; and
    calculating an Output per UOA-ID per time segment to generate said at least one Output Expression.

11. A system for improving resource allocation using a plurality of sets of information the system comprising:
    system software; and
    a central processing unit for implementing said system software, wherein said system software operates to perform the method comprising the steps of:
    for each set of information, identifying a particular Individual Unit of Analysis UOA-ID), a specific population, a Calendar Clock date/time for each UOA-ID (CCT) and a Variable Value (VAR);

grouping each UOA-ID into an appropriate Grouper;
identifying a Start Time wherein said Start Time is the earliest CCT for each specific UOA-ID per said specific population (Type);
identifying a time segment duration;
forming time segments based on the Start Time wherein each UOA-ID meet a certain eligibility criteria;
adjusting and standardizing each VAR to create Eligible Adjusted Variable Values (AdjVAR Values);
placing each AdjVAR Value into the appropriate time segment;
calculating an eligibility score for each UOA-ID; and
generating an Output Expression for analyzing and evaluating a resource allocation showing at least one trend of a particular population, said at least one trend expressed in at least one of said Cohort time segments and wherein said at least one Output Expression is based on said Eligible Adjusted Variable Value and said UOA-ID for each said Cohort time segment;
and wherein the system further includes analyzing and evaluating a resource allocation utilizing the generated said at least one Output Expression.

12. The method of claim 11 further comprising the step of transforming the Output Expression from expressed in Cohort time segments to being expressed in CCT segments.

13. The system of claim 11 wherein said at least one trend relates to the viewing time of an advertisement.

14. The system of claim 11 wherein said at least one trend relates to the length of viewing time of an advertisement by a consumer.

15. The system of claim 11 wherein said at least one trend relates to the health care industry.

16. The system of claim 11 wherein said at least one trend relates to the group consisting of marketing applications, trademark applications, and health care applications.

17. The method of claim 11 further comprising the step of calculating an Eligible Adjusted Variable Value (EAV) based on a summary metric for each UOA-ID per Type.

18. The method of claim 11 further comprising the steps of:
determining a Dichotomous Variable (DV) per Type per time segment;
calculating an Eligible Adjusted Variable Value (EAV) summary metric for all UOA-IDs per Type per time segment; and
calculating an EAV Net Value per Type per time segment to generate said at least one Output Expression.

19. The method of claim 11 further comprising the steps of:
determining a Return On Resource Allocation (RORA);
determining an Outcome;
calculating a Number Needed To Target (NNT);
calculating an Eligible Adjusted Variable Value (EAV) Net Value per Type per time segment; and
calculating the maximum available Resource Allocation (RA) per UOA-ID per time segment to generate said at least one Output Expression.

20. The method of claim 11 further comprising the steps of:
determining a Resource Allocation (RA);
determining an Outcome;
calculating a Number Needed To Target (NNT);
calculating an Eligible Adjusted Variable Value (EAV) Net Value per Type per time segment; and
calculating a Return On Resource Allocation (RORA) per UOA-ID per time segment to generate said at least one Output Expression.

21. The method of claim 11 further comprising-the steps of:
determining a Return On Resource Allocation (RORA);
determining a Resource Allocation (RA);
calculating a Number Needed To Target (NNT);
calculating an Eligible Adjusted Variable Value (EAV) New Value per Type per time segment; and
calculating an Output per UOA-ID per time segment to generate said at least one Output Expression.

22. A system for performing a study of analyzing and evaluating resource allocation comprising:
system software; and
a central processing unit for implementing said system software, wherein said system software operates to perform the method of identifying a set of information, each set comprising a unit of analysis (UOA), a particular Individual Unit of Analysis entity involved in the study (UOA-ID), a Type, a Calendar Clock date/time (CCT), and a Variable Value (VAR Value);
grouping each UOA-ID into an appropriate Grouper;
organizing each UOA-ID within each Grouper by succeeding CCT;
identifying a Start Time wherein each UOA-ID meets all of the eligibility criteria to be included into a Population;
forming time segments based on the Start Time;
adjusting and standardize each VAR Value to create Adjusted Variable Value (AdjVAR Values);
sorting and placing each AdjVAR Value into the appropriate time segments;
calculating an Eligibility Score for each UOA-ID;
calculating an Eligible Adjusted Variable Value (EAV) for each time segment;
generating at least one Output Expression showing at least one trend of a particular population, said at least one trend expressed in at least one of said Cohort time segments and wherein said at least one Output Expression is based on said Eligible Adjusted Variable Value and said UOA-ID for each said Cohort time segment;
and wherein the system further includes analyzing and evaluating a resource allocation utilizing the generated said at least one Output Expression.

23. The system of claim 22 wherein said at least one Output Expression displays trends in health care.

24. A system for use by a user in analyzing resource allocation comprising:
a central processing unit for operating software effective for performing the method of:
identifying at least one criterion for a Population;
identifying sets of information wherein each set of information includes a particular Individual Unit of Analysis entity involved in a study (UOA-ID), a Calendar Clock Date/time (CCT), and a Variable Value (VAR Value);
grouping each UOA-ID into an appropriate Type;
identifying a Start Time wherein each UOA-ID meets all of the eligibility criteria to be included into the Population;
forming at least one Cohort Time segment based on the Start Time;
placing the VAR Value into the appropriate time segment;
calculating an eligibility score for each UOA-ID for each time segment;
calculating an Eligible Adjusted Variable Value; and
generating an Output Expression showing at least one trend of the Population, said at least one trend expressed in at least one of said Cohort time segments and wherein said at least one Output Expression is based on said Eligible Adjusted Variable Value and said UOA-ID for each said Cohort time segment.

25. The system of claim 24 wherein said system is used for applications selected from the group consisting of marketing applications, trademark applications, and health care applications.

26. A central processing unit having software that operates to create at least one Output Expression comprising a representation of Eligible Adjusted Variable Value (EAV) trends for a particular Population having an eligibility criteria and formed from taking individual units from sets of date wherein each individual unit meets at least one defined criteria, said EAV trends are expressed in Cohort time segments based on a Start Time wherein each individual unit meets all of the eligibility criteria to be included into the Population; and of Number Needed To Target (NNT) trends of a particular Population; said trends are expressed in Cohort time segments.

* * * * *